(12) United States Patent
Ciarrocca (10) Patent No.: US 7,195,630 B2
(45) Date of Patent: Mar. 27, 2007

(54) CONVERTING CUTTING AND COAGULATING ELECTROSURGICAL DEVICE AND METHOD

(75) Inventor: Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 328 days.

(21) Appl. No.: 10/645,810

(22) Filed: Aug. 21, 2003

(65) Prior Publication Data
US 2005/0043728 A1 Feb. 24, 2005

(51) Int. Cl.
*A61B 18/18* (2006.01)
(52) U.S. Cl. .................................. 606/48; 128/898
(58) Field of Classification Search ............ 606/27–52, 606/48, 45–50, 41
See application file for complete search history.

(56) References Cited

U.S. PATENT DOCUMENTS 4,911,159 A * 3/1990 Johnson et al. ............... 606/37
5,098,430 A * 3/1992 Fleenor ......................... 606/42
5,472,442 A * 12/1995 Klicek .......................... 606/42
5,697,281 A 12/1997 Eggers et al.
6,666,864 B2 * 12/2003 Bencini et al. ............... 606/41

* cited by examiner

*Primary Examiner*—Roy D. Gibson
*Assistant Examiner*—Pete Vrettakos (57) ABSTRACT

A bipolar electrosurgical instrument and method for use is provided. The instrument includes a handle at a proximal end, active and return electrodes at a distal end that are electrically insulated from one another, a shaft extending therebetween, and a converting element including an electrically conductive portion. The converting element is movable between a first position wherein the electrically conductive portion is in electrical contact with the active electrode and not the return electrode, and a second position wherein the electrically conductive portion is not in electrical contact with the active electrode.

17 Claims, 6 Drawing Sheets

CONVERTING CUTTING AND COAGULATING ELECTROSURGICAL DEVICE AND METHOD

FIELD OF THE INVENTION

This invention relates generally to bipolar electrosurgical instruments, and in particular to convertible cutting and coagulating bipolar RF electrodes that are readily convertible between efficient cutting and coagulating modes of operation.

DESCRIPTION OF THE BACKGROUND ART

Electrosurgical instruments and techniques are widely used in surgical procedures because they generally reduce patient bleeding and trauma associated with cutting operations as compared with mechanical cutting instruments and the like. Conventional electrosurgical technologies may be classified as being monopolar or bipolar. Monopolar techniques rely on external grounding of the patient, where the surgical device defines only a single electrode pole. Thus, the electric current must pass through the patient to reach the external grounding pad. Bipolar devices have two electrodes that are located in proximity to one another for the application of current between their surfaces. By being located in proximity to one another, bipolar devices have the advantage that current need not be passed through the body, but rather only between the two electrodes.

Conventional bipolar devices are commonly used to maintain or create hemostasis. Electrosurgical energy passing between the electrode poles and through tissue arranged between them promotes coagulation and thereby reduces bleeding. A historic limitation of these devices has been their inability to cut tissue, which greatly limits their utility.

Recently, RF bipolar generators and tools have been developed that cut tissue through the use of plasma. These systems employ a conductive fluid supply which is converted to a plasma 'bubble' on a portion of the electrode tip through the application of RF electrosurgical current. Tissue that contacts the plasma bubble experiences rapid vaporization of its cellular fluid, thereby producing a cutting effect.

Creation of a plasma 'bubble' in the conductive fluid media at the electrode tip requires a very high current density. As such, unlike conventional bipolar instruments, the electrode poles on these devices are not of generally the same size. Rather, one of the poles (generally referred to as the active electrode) is significantly smaller than the other pole (generally referred to as the return electrode). This configuration allows for current density sufficient to form plasma only at the active pole.

When driven at reduced voltage levels that are not sufficient to form and maintain a plasma bubble, these devices can function in a fashion similar to conventional bipolar devices to direct current through a defined area of tissue. Unfortunately, the physical arrangement of the electrodes on these instruments generally limits their capacity for coagulating tissue. In particular, having a small active electrode relative to a large return electrode concentrates current at the small active electrode, which is less than optimal for coagulation where it is desirable to effect a larger lesion or area of tissue coagulation.

It would thus be desirable to provide an improved bipolar electrosurgical instrument that functions effectively as both a cutting and a coagulating instrument.

SUMMARY OF THE INVENTION

A bipolar electrosurgical instrument is provided including a handle at a proximal end, active and return electrodes at a distal end electrically insulated from one another, a shaft extending between the handle and the distal end, and a converting element including an electrically conductive portion. The converting element is movable between a first position wherein the electrically conductive portion is in electrical contact with the active electrode and not the return electrode, and a second position wherein the electrically conductive portion is not in electrical contact with the active electrode. According to one embodiment, when in the second position, the converting element is in electrical contact with the return electrode. In yet another embodiment, when in the first position, the surface area of the active electrode in combination with the electrically conductive portion of the converting electrode is comparable to the surface area of the return electrode. In a further embodiment, when in the second position, the surface area of the active electrode is less than the surface area of the return electrode, and in yet another embodiment, when in the second position the converting element is in electrical contact with the return electrode and forms part of the return electrode.

In another embodiment, the instrument further includes an activating element disposed on the handle that is movable between a first position and a second position. The activating element is coupled to the converting element such that moving the activating element between the first and second position moves the converting element between the converting element's first and second positions respectively.

In an alternate embodiment, the electrically conductive portion of the converting element is concentrically disposed about the active electrode.

The instrument may also further include an insulating member concentrically disposed about a portion of the active electrode between the active electrode and the converting element, but exposing a tip portion of the active electrode. When the converting element is in the second position the insulting member entirely insulates the active electrode from the electrically conductive portion of the converting element, and when the converting element is in the first position, the insulting member does not entirely insulate the active element from the electrically conductive portion of the converting element.

In another embodiment, the instrument further includes a fluid delivery channel extending between a fluid inlet at the proximal end of the instrument and one or more fluid outlets disposed in proximity to the active electrode, and in yet another embodiment, the instrument further includes a vacuum delivery system extending between a vacuum inlet at the proximal end of the instrument and one or more vacuum outlets disposed in proximity to the active electrode.

The instrument may include a plurality of active electrodes and at least one return electrode, and may be electrically coupled to an electrosurgical generator for providing electrosurgical energy to the active electrodes.

Also provided is a bipolar electrosurgical instrument having a handle at a proximal end, active and return electrodes at a distal end electrically insulated from one another, a shaft extending between the handle and the distal end, and means for changing an effective surface area ratio of the active electrode relative to the return electrode. In one embodiment the means for changing further includes a converting element having an electrically conductive portion. The converting element is movable between a first position wherein it is in electrical contact with the active electrode and not the return electrode, and a second position wherein it is not in electrical contact with the active electrode.

A method is also provided for electrosurgically treating target tissue. The method includes providing an electrosurgical instrument having active and return electrodes at a distal end that are electrically insulated from one another, and a converting element having an electrically conductive portion. The converting element is movable between a first position and a second position wherein in the first position the electrically conductive portion of the converting element is in electrical contact with the active electrode to thereby increase an effective surface area of the active electrode relative to when it is in the second position. The method further includes treating a first target tissue with the converting element in the first or second position, moving the converting element to the other one of the first or second positions, and treating a second target tissue with the converting element in the other one of the first or second positions. In one embodiment, the first and second target tissues are the same tissue, whereas in an alternate embodiment, the first and second target tissues are different.

Further, according to one embodiment, when the instrument is in the second position the instrument is better suited to cut or vaporize tissue than in the first position. In yet another embodiment, when the instrument is in the first position the instrument is better suited to coagulate tissue than in the second position. In yet another embodiment, the method further includes delivering an electrically conductive fluid to the tissue while treating the tissue with the converting element in the second position.

A method is also provided for electrosurgically treating tissue including providing an electrosurgical instrument having active and return electrodes at a distal end and a means for changing an effective surface area ratio of the active electrode relative to the return electrode, treating tissue using the instrument with a first surface area ratio of the active electrode relative to the return electrode, using the means for changing to change to a second surface area ratio of the active electrode relative to the return electrode, and treating tissue using the instrument with the second surface area ratio.

For a further understanding of the nature and advantages of the present invention, reference should be made to the following description taken in conjunction with the accompanying drawings.

BRIEF DESCRIPTION OF THE DRAWINGS

FIGS. 5a and 5b through 9a and 9b illustrate alternative tip designs for the electrosurgical instrument of the present invention.

DETAILED DESCRIPTION OF THE INVENTION

Before explaining the present invention in detail, it should be noted that the invention is not limited in its application or use to the details of construction and arrangement of parts illustrated in the accompanying drawings and set forth in the description. Other embodiments, variations and modifications are possible without departing from the spirit and scope of the invention. Furthermore, unless otherwise indicated, the terms and expressions employed herein have been chosen for the purpose of describing the illustrative embodiments of the present invention for the convenience of the reader and are not for the purpose of limiting the invention.

Figure 1:
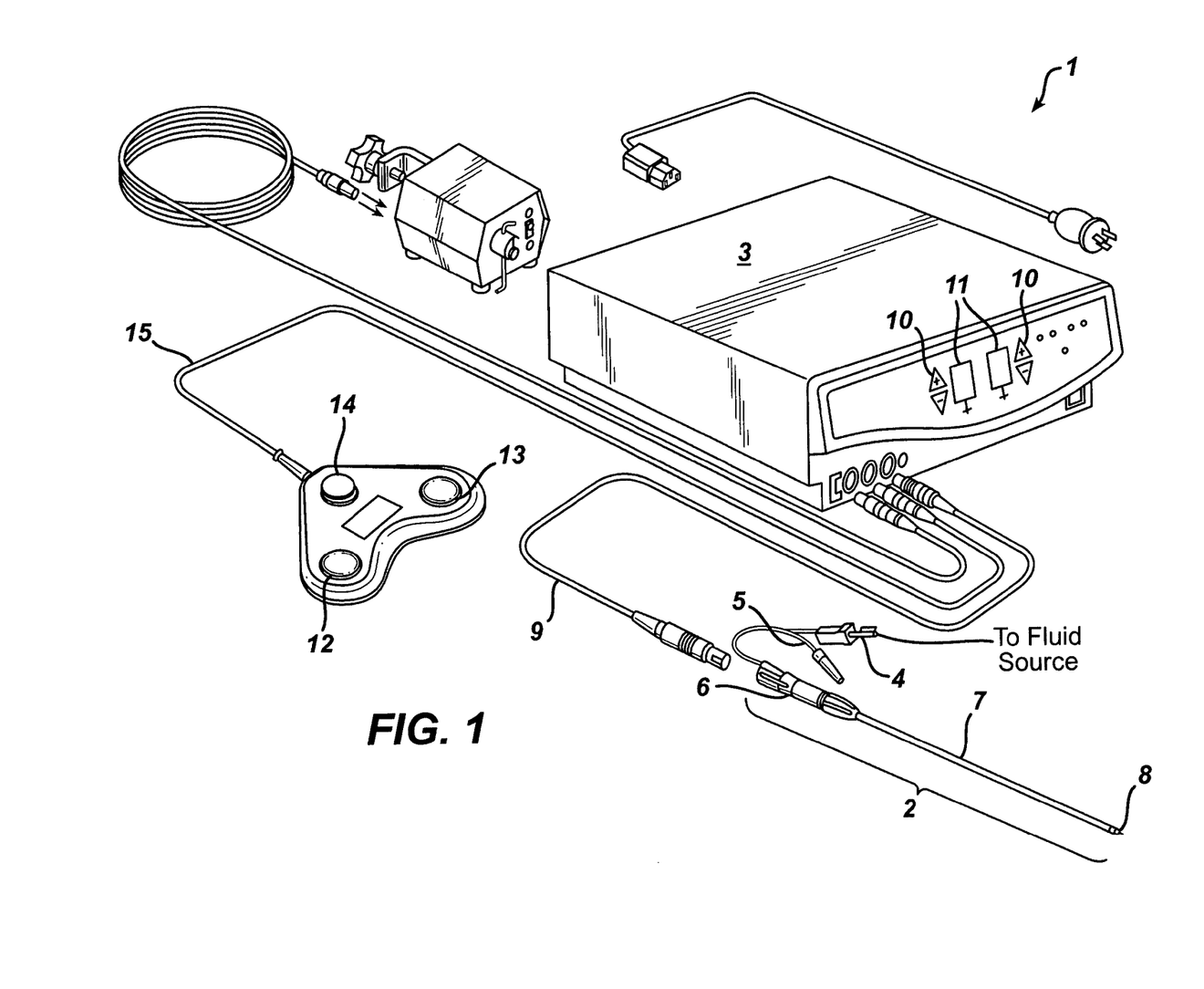
FIG. 1 is a perspective view of an electrosurgical system according to the present disclosure incorporating a power supply and an electrosurgical instrument for treating target tissue of a patient.

Referring now to FIGS. 1–10, an exemplary electrosurgical system will now be described in detail. As shown in FIG. 1, an exemplary electrosurgical system 1 generally comprises an electrosurgical instrument 2 connected to a power supply 3 for providing high frequency voltage, and a fluid coupler 4 for coupling with a fluid source (not shown) for supplying electrically conductive fluid, such as saline, to the instrument. In addition, the electrosurgical system may include an endoscope (not shown) with a fiber optic light for viewing the surgical site. The endoscope may be integral with instrument 2, or it may be part of a separate instrument. The system 1 may also include a vacuum source (not shown) for coupling to a suction lumen or tube 5 in the instrument for aspirating the target site.

The electrosurgical instrument 2 generally includes a handle 6 at a proximal end, one or more bipolar electrode pairs at its distal end, and an elongate shaft 7 extending therebetween. A removable connecting cable 9 electrically couples the electrode elements to power supply 3 via a connector housed in handle 6 and conductors contained within or integral to the assembly of the instrument.

Power supply 3 has operator controllable voltage level adjustments 10 to change the applied voltage level, which is observable at the voltage level displays 11. Power supply 3 also includes first, second, and third foot pedals 12, 13, 14 and a cable 15 which is removably coupled to power supply 3. The foot pedals allow the surgeon to remotely adjust the energy level applied to the active electrodes and activate different modes of operation. In an exemplary embodiment, first foot pedal 12 is used to place the power supply into the "ablation", "vaporization", or "cutting" mode (dependent on specifics of instrument design), second foot pedal 13 is used to place the power supply into the "coagulation" mode, and the third foot pedal 14 allows the user to adjust the voltage level within the ablation mode. In the ablation mode, a sufficient voltage is supplied to the electrode pair to establish the requisite conditions for molecular dissociation of the tissue in the area of the active electrode element (i.e., vaporizing a portion of the electrically conductive fluid, ionizing the vapor layer, and accelerating charged particles against the tissue). The requisite level for ablation will vary depending on the number, size, shape, position and spacing of the electrode elements. In the coagulation mode, the power supply 3 applies low enough voltage across the active electrodes to avoid vaporization of the electrically conductive fluid and subsequent molecular dissociation of the tissue. Instead, current will be directed between the electrode elements through the conductive fluid and tissue in contact with them. Additional details regarding the electrosurgical system described above can be found in U.S. Pat. No. 5,697,281, which is incorporated herein by reference in its entirety.

Figure 2:
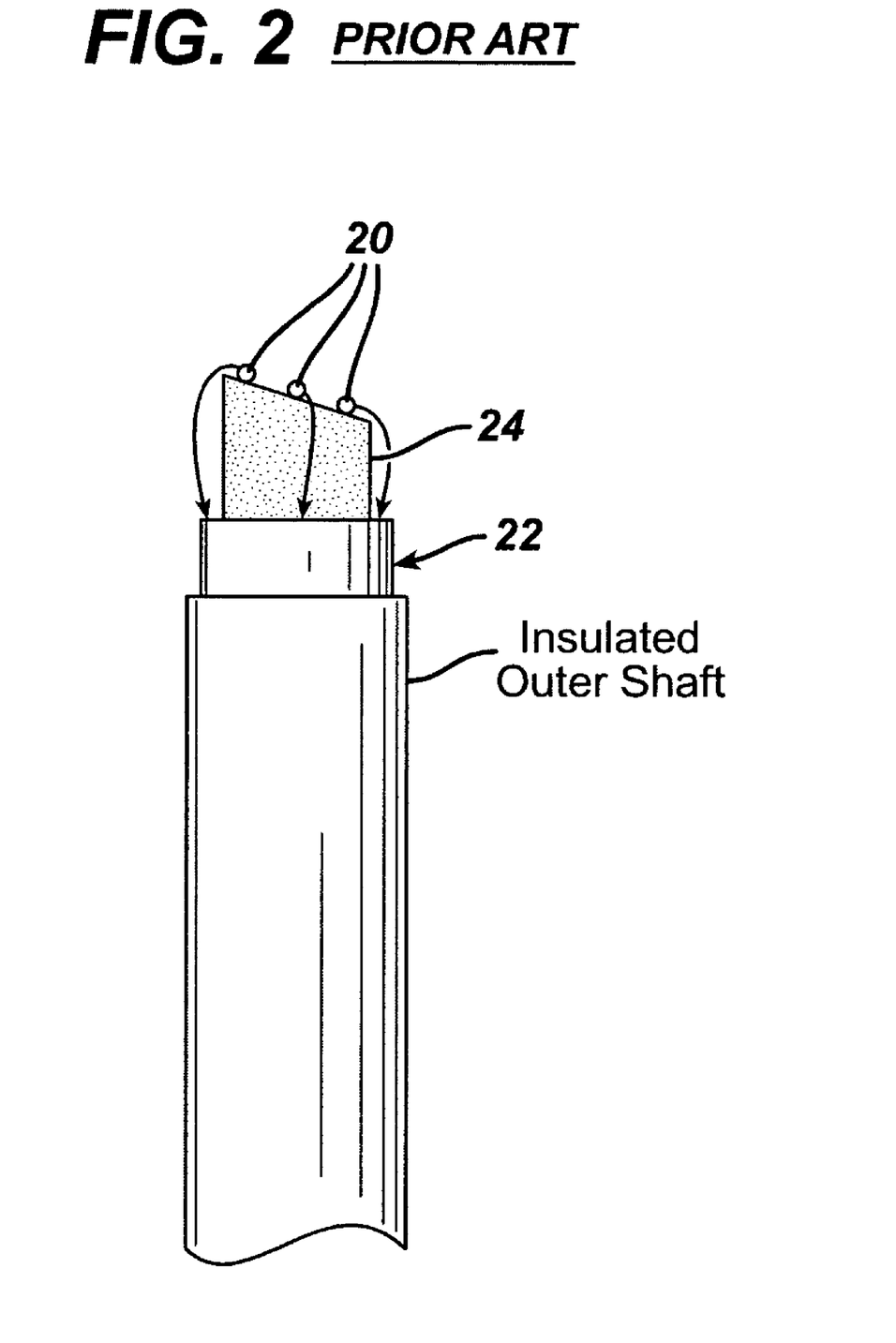
FIG. 2 is a side view of a tip of an exemplary prior-art bipolar electrosurgical electrode designed for use with the electrosurgical system shown in FIG. 1.

As indicated above, known prior art devices that allow power to be adjusted between a vaporization or cutting mode and a coagulation mode have a uniform tip design for both modes, generally resulting in sub-optimal performance in at least one such mode. FIG. 2 shows one such distal tip configuration that can be used in conjunction with the system previously described. Arranged at the distal tip of this instrument are active electrodes 20 and a common return element 22. These elements are fixably arranged with an insulating member 24 between them and the geometry of these pairs cannot be altered by the user to suit a particular surgical need. As such, instruments constructed in this fashion may be well suited for cutting or ablation but less suitable for coagulation. Conversely, instruments that are proficient coagulators may be inefficient cutters or ablators. As stated above, optimal performance in a cutting mode calls for an active electrode(s) that has a much smaller surface area than the return electrode, whereas optimal performance in a coagulation mode calls for an active and return electrode(s) that have generally the same size surface area.

Figure 3:
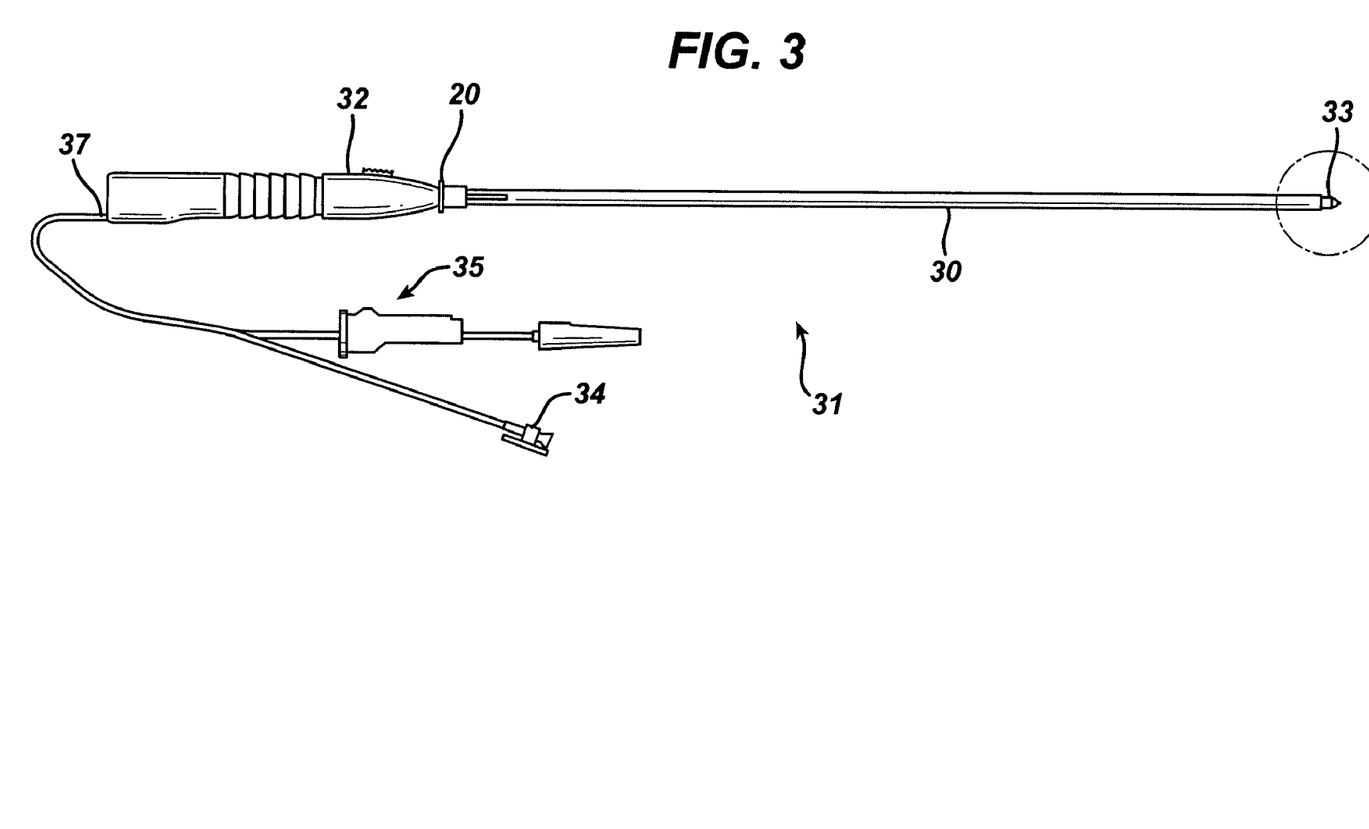
FIG. 3 is a side view of an electrosurgical instrument according to the present disclosure.

FIG. 3. shows an electrosurgical instrument 31 of the present invention that can be used with an electrosurgery system as previously described. The instrument generally includes a handle 32 at a proximal end, active and return electrodes at a distal end 33 (described in greater detail below), and an elongate shaft 30 extending therebetween. The elongate shaft may be flexible or rigid, may be a fiberglass composite, or comprise a plastic material that is easily molded into a desired shape, or be constructed from an electrically conducting metal. In the latter case, shaft 30 includes an electrically insulating jacket, which is typically formed as one or more electrically insulating sheaths or coatings, such as polytetrafluoroethylene, polyamide, and the like. The provision of electrically insulated jacket over the shaft prevents direct electrical contact between the metal shaft and any adjacent body structure or the surgeon which could result in unwanted heating and necrosis of the structure at the point of contact and/or sub-optimal device performance.

Handle 30 typically comprises a plastic material that is easily molded into a suitable shape for handling by the surgeons. Handle 32 defines an inner cavity (not shown) that houses an electrical connector which provides a suitable interface for coupling instrument 31 to the power supply via an electrical conducting cable. A fluid coupler 34 is coupled to the proximal end of the handle and provides a means for coupling to a conductive fluid source (not shown) which is required for plasma mode operation. Similarly, a suction lumen or tube device 35 is coupled to the proximal end of the handle and provides a means for coupling to a vacuum source for the removal of fluid from the surgical site and/or control of the flow of fluid around the electrode elements.

Incorporated within or just distal to the handle is a sliding mechanism that is directly coupled to the converting element of the device through a slot in the outer shaft of the instrument. Axial movement of this sliding mechanism results in reconfiguration of the distal tip of the instrument between cutting and coagulating modes as described in greater detail below.

Figure 4A:
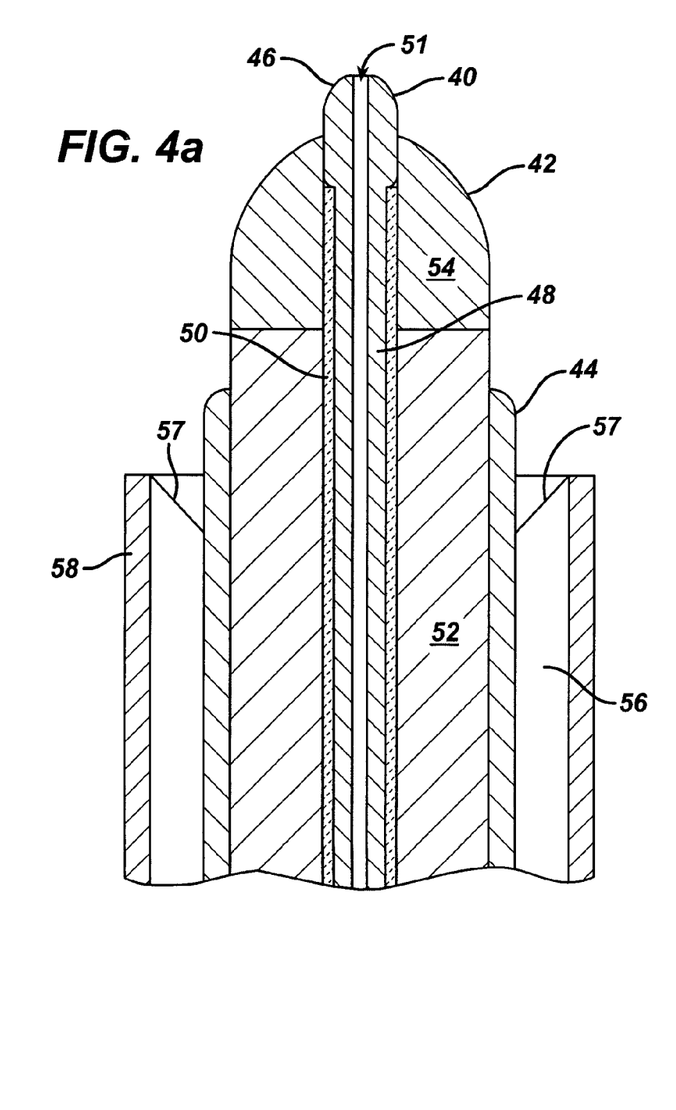
FIGS. 4a and 4b are cross-sectional views of the distal tip of an electrosurgical instrument according to the present invention in the coagulating and cutting positions respectively.
Figure 4B:
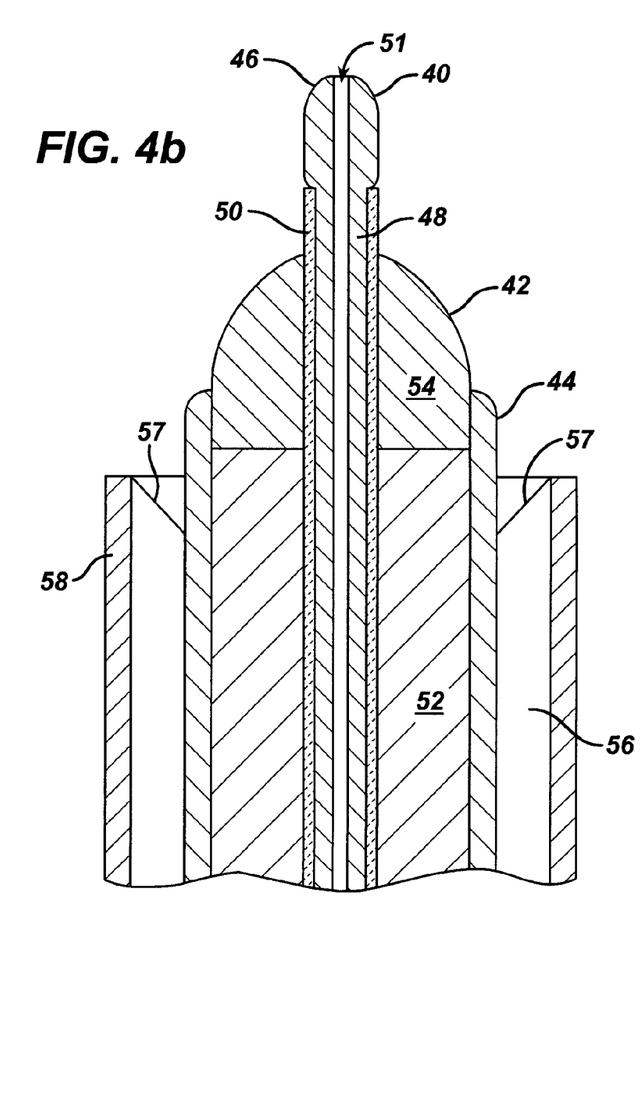

FIGS. 4a and 4b illustrate in greater detail the distal tip 33 of the instrument 31. In a preferred embodiment, the instrument is constructed of three concentric elements of generally circular cross-section. These elements are hereafter referred to as the active electrode structure 40, the converting element 42, and the return electrode structure 44.

The active electrode structure 40 is fixed in axial position relative to the handle and is made from an appropriate conductive metal. In the embodiment illustrated in FIGS. 4a and 4b, the active electrode 40 is substantially circular in cross-section. The distal tip 46 of this element forms the fixed active portion of the bipolar electrode pair. Although a variety of conductive materials such as steel or copper are suitable for making the length of this element, the distal tip must be constructed from a metal that can withstand the heat required for electrosurgical application, such as tungsten and its alloys, molybdenum and its alloys, or platinum and its alloys. A portion of the active electrode structure proximal to the distal tip possesses an area of reduced diameter 48. In this area, an electrically insulating material 50 such as ceramic, glass, plastic, or silicone surrounds the element, thus preventing electrical connection to the element in this area. The center of this element may be hollow to allow for connection to a source of regulated vacuum to allow removal of excess fluid from the surgical site and to control the flow of conductive fluid around the electrode elements.

The converting element 42 serves to convert the instrument between one that is optimized for cutting and one that is optimized for coagulating, and is axially movable within the instrument shaft between the extended and retracted positions shown in FIGS. 4a and 4b respectively. In the illustrated embodiment, the converting element is also substantially circular in cross-section, and is concentrically positioned to surround the active electrode. A first portion 52 of the converting element is made from an insulating material such as plastic or ceramic, or alternatively from a conductive material which is bilaterally insulated along its length. The distal end portion 54 of the converting element is made of an electrically conductive material such as tungsten metal or its alloys, stainless steel alloys, platinum or its alloys, or molybdenum or its alloys. Within or around the outside of this element may be one or more lumens 56 having outlets 57 for delivering or removing conductive media to the distal tip or the instrument. These lumens may possess multiple outlets at their distal tips to allow proper fluid delivery in either electrode configuration. These lumens extend through the instrument from a fluid inlet at the proximal end (location shown generally by reference numeral 37 of FIG. 3), which is in fluid communication with the fluid coupler 34 that itself can be coupled to a fluid source. Lumens that remove fluid from the vicinity of the active electrode form part of a vacuum deliver channel 51 that similarly extends along the length of the instrument between an inlet and outlet. The inlet can be coupled, via a vacuum coupler 35, to a vacuum source.

Referring back to the converting element, when in the retracted or "cutting" position shown in FIG. 4b, the distal end portion 54 of the converting element is preferably in electrical contact with the return electrode structure 44, thus causing it to function as part of return portion of the bipolar electrode and thus increasing the effective surface area of the return electrode. The aforementioned insulation 50 that surrounds a portion of the active electrode proximal to the tip of the active electrode structure prevents the converting element from achieving electrical contact with the active electrode member in this position. Thus, in this configuration, the surface area of the active portion of the bipolar electrode pair is significantly lower than that of the return portion, thereby concentrating the current at the small active electrode and allowing the instrument to better act as a cutting or vaporizing device.

In the illustrated embodiment, the return electrode structure 44 is concentrically positioned around the converting element 42, and consists of a metal that can be similar to that used for the distal end portion of the active electrode. Along most of its length, an insulating member 58 is concentrically positioned around the return electrode and fluid lumen structures.

When in the extended or "coagulating" position shown in FIG. 4a, the converting element is in electrical contact with the active electrode structure, but not in electrical contact with the return electrode, thus greatly increasing the surface area of the active portion of the bipolar electrode pair. In this configuration, the surface area of the active portion of the bipolar electrode pair is similar to that of the return portion, thus causing the instrument to perform better as a coagulating device.

Figure 5A:
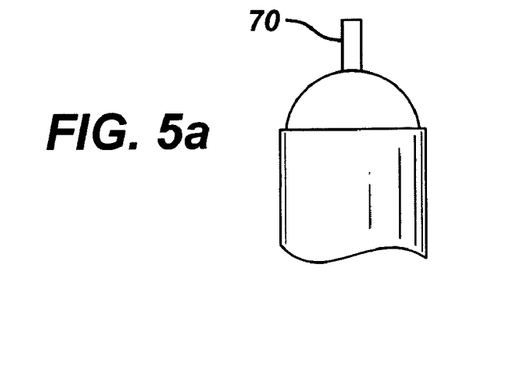
Figure 5B:
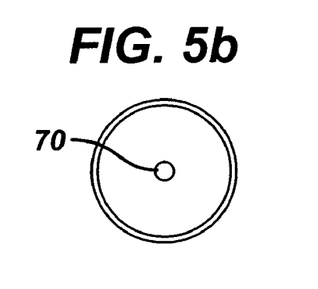
Figure 6A:
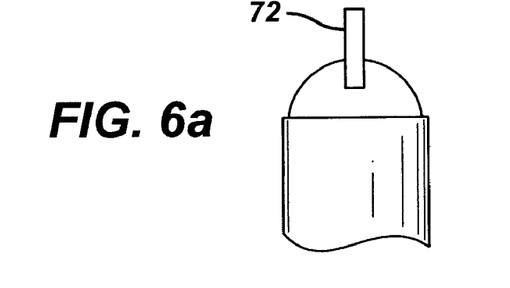
Figure 6B:
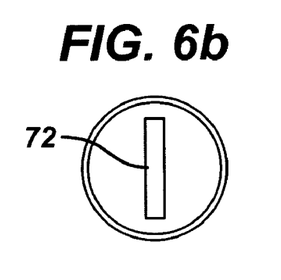
Figure 7A:
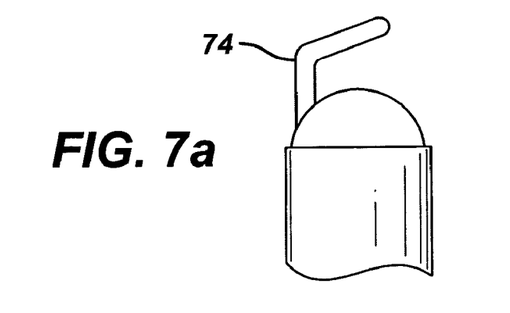
Figure 7B:
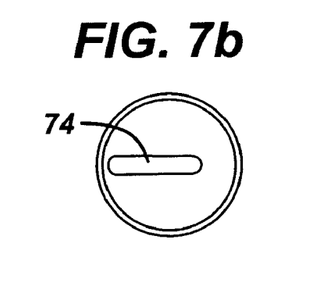
Figure 8A:
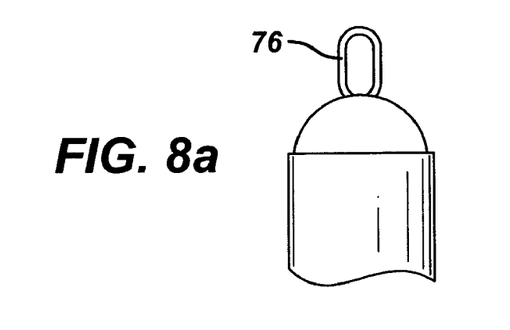
Figure 8B:
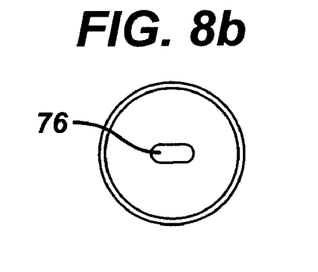
Figure 9A:
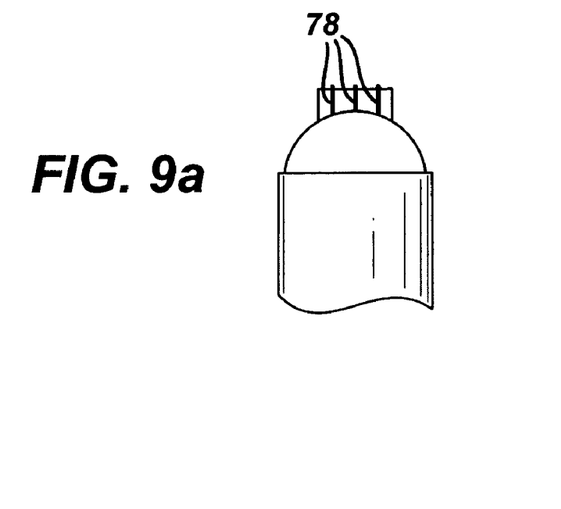
Figure 9B:
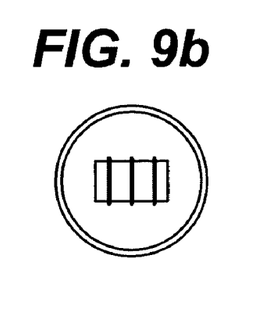

Although one particular embodiment has been described in detail above, it is to be understood that multiple different configurations of the distal tip are possible. FIGS. 5a–9b illustrate several of such alternate embodiments. FIGS. 5a and 5b illustrate a needle design wherein the active electrode 70 is essentially a cylinder. FIGS. 6a and 6bb illustrate a knife or blade design in which the active electrode 72 is a squared or rounded rectangular blade. FIGS. 7a and 7a illustrate a hook design in which the active electrode 74 possesses a bend of some angle, preferably between 14 and 45 degrees. FIGS. 8a and 8b illustrate a loop design in which the active electrode 76 is a wire loop. FIGS. 9a and 9b illustrates a vaporizing design in which the active electrode 78 is formed from a series of wires mounted and spaced on an insulating substrate in a manner similar to that shown in FIG. 2. It is understood that the opening in the distal tip of the converting element can and will be varied to accommodate axial passage around these various active electrode shapes.

Figure 10A:
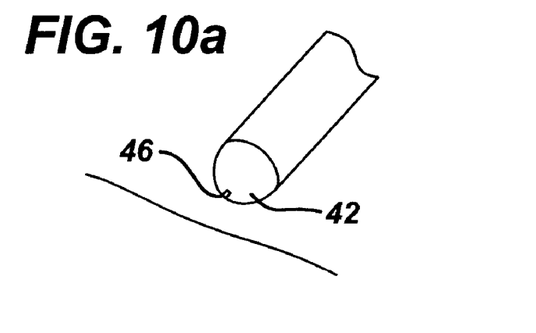
FIGS. 10a through 10d illustrate the steps of a method for using an electrosurgical instrument of the present disclosure.
Figure 10B:
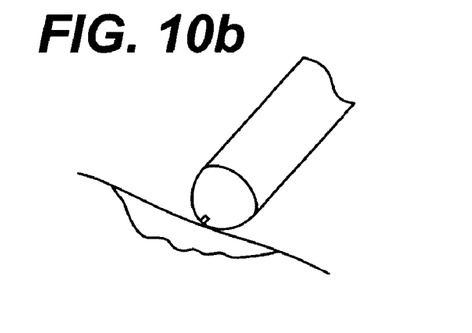
Figure 10C:
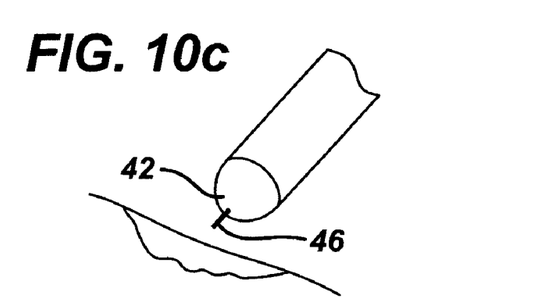
Figure 10D:
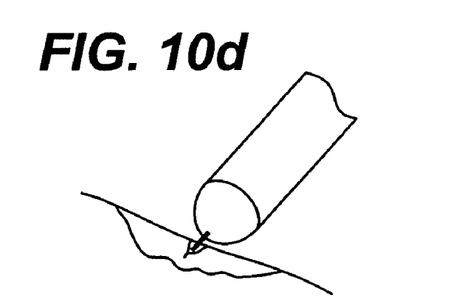

FIGS. 10a–10d schematically represent typical steps involved in a method for using the electrosurgical system and instrument described herein to treat a patient. FIG. 10a shows the distal tip of an instrument with the converting member 42 in the extended position (as shown in FIG. 4a) to thereby optimize the use of the instrument for coagulating tissue. FIG. 10b shows the instrument being activated while placed against or in very close proximity to the target area of tissue, causing the tissue to be coagulated or desiccated. FIG. 10c shows the instrument removed from the treatment site and the converting element 42 retracted (as in FIG. 4b) for optimal cutting or vaporization. In this form the converting element is electrically in contact with the return electrode element as described above, so that the surface area of the active element is significantly less than that of the return element. FIG. 10d shows the electrode cutting the area of treated tissue.

Although exemplary embodiments and methods for use have been described in detail above, those skilled in the art will understand that many variations are possible without departing from the spirit and scope of the invention, which is limited only by the appended claims.

What is claimed is:

1. A bipolar electrosurgical instrument, comprising:
   a handle at a proximal end;
   an active electrode electrically coupled to an electrosurgical generator for providing electrosurgical energy thereto and a return electrodes said active and return electrodes being located at a distal end of the instrument and electrically insulated from one another;
   a shaft extending between the handle and the distal end;
   a converting element including an electrically conductive portion, the converting element being slidably movable between a first extended position wherein the electrically conductive portion is in electrical contact with the active electrode and not the return electrode so as to form part of the active electrode and thereby increase an effective surface area of the active electrode relative to the return electrode, and a second retracted position wherein the electrically conductive portion is not in electrical contact with the active electrode to thereby decrease the effective surface area of the active electrode relative to the return electrode as compared to the first position, wherein the instrument uses bipolar energy applied by the electrosurgical generator to the active electrode in both the first and second positions.

2. The instrument according to claim 1, wherein in the first position, the effective surface area of the active electrode relative to the return electrode is substantially greater than in the second position.

3. The instrument according to claim 1, wherein in the second position, a surface area of the active electrode is less than a surface area of the return electrode.

4. The instrument according to claim 3, wherein in the second position the converting element is in electrical contact with the return electrode and forms part of the return electrode.

5. The instrument according to claim 1, further comprising an activating element disposed on the handle and being movable between a first position and a second position, the activating element being coupled to the converting element such that moving the activating element between the first and second position moves the converting element between the converting element first and second positions respectively.

6. The instrument according to claim 1, wherein the electrically conductive portion of the converting element is concentrically disposed about the active electrode.

7. A bipolar electrosurgical instrument, comprising:
   a handle at a proximal end;
   active and return electrodes at a distal end electrically insulated from one another;
   a shaft extending between the handle and the distal end;
   a converting element including an electrically conductive portion, the converting element being slidably movable between a first extended position wherein the electrically conductive portion is in electrical contact with the active electrode and not the return electrode so as to form part of the active electrode and thereby increase an effective surface area of the active electrode relative to the return electrode, and a second retracted position wherein the electrically conductive portion is not in electrical contact with the active electrode to thereby decrease the effective surface area of the active electrode relative to the return electrode as compared to the first position, wherein the instrument uses bipolar energy in both the first and second positions, and
   an insulating member concentrically disposed about a portion of the active electrode between the active electrode and the converting element but exposing a tip portion of the active electrode, wherein when the converting element is in the second position the insulting member entirely insulates the active electrode from the electrically conductive portion of the converting element, and wherein when the converting element is in the first position, the insulating member does not entirely insulate the active element from the electrically conductive portion of the converting element.

8. The instrument according to claim 1, further comprising a fluid delivery channel extending between a fluid inlet at the proximal end of the instrument and at least one fluid outlet disposed in proximity to the active electrode.

9. The instrument according to claim 1, further comprising a vacuum delivery system extending between a vacuum inlet at the proximal end of the instrument and at least one vacuum outlet disposed in proximity to the active electrode.

10. The instrument of claim 1, further comprising a plurality of active electrodes and at least one return electrode.

11. A bipolar electrosurgical instrument, comprising:
a handle at a proximal end;
an active electrode electrically coupled to an electrosurgical generator for providing electrosurgical energy thereto and a return electrode, wherein the active and return electrodes are located at a distal end of the instrument and electrically insulated from one another;
a shaft extending between the handle and the distal end; and
means for changing an effective surface area ratio of the active electrode relative to the return electrode by slidably moving a conductive converting element between a first extended position wherein it is in electrical contact with and forms part of the active electrode and is not in electrical contact with the return electrode, and a second retracted position wherein it is not in electrical contact with and does not form part of the active electrode, and wherein bipolar energy can be applied to the active electrode when the converting element is in both the first and second positions.

12. A method for electrosurgically treating target tissue, comprising:
providing a bipolar electrosurgical instrument having an active electrode electrically coupled to an electrosurgical generator for supplying electrosurgical energy thereto and return electrode, the active and return electrodes being located at a distal end of the instrument and being electrically insulated from one another, and a converting element having an electrically conductive portion, the converting element being movable between a first extended position and a second retracted position wherein in the first position the electrically conductive portion of the converting element is in electrical contact with and forms part of the active electrode and wherein in the second position the electrically conductive portion is not in electrical contact with the active electrode, so that when in the first position an effective surface area of the active electrode is greater than in the second position;
using bipolar energy applied to the active electrode by the electrosurgical generator to treat a first target tissue with the converting element in the first or second position;
moving the converting element to the other one of the first or second positions; and
using bipolar energy applied to the active electrode by the electrosurgical generator to treat a second target tissue with the converting element in the other one of the first or second positions.

13. The method according to claim 12, wherein the first and second target tissues are the same tissue.

14. The method according to claim 12, wherein the first and second target tissues are different.

15. The method according to claim 12, wherein when the instrument is in the second position the instrument is capable of cutting or vaporizing tissue when electrosurgical energy is applied to the active electrode, and wherein when the instrument is in the first position the instrument is capable of coagulating tissue when electrosurgical energy is applied to the active electrode.

16. The method according to claim 12, further comprising:
delivering an electrically conductive fluid to the vicinity of the active electrode while treating the tissue with the converting element in the second position.

17. A method for electrosurgically treating tissue comprising:
providing a bipolar electrosurgical instrument having an active electrode electrically coupled to a power source and a return electrode, the active and return electrodes being located at a distal end, and a means for changing an effective surface area ratio of the active electrode relative to the return electrode, the means for changing being slidable between a first extended position wherein an electrically conductive portion of said means for changing is in electrical contact with and forms part of the active electrode, and a second retracted position wherein the electrically conductive portion is not in electrical contact with and does not form part of the active electrode;
using bipolar energy applied to the active electrode by the electrosurgical generator to treat tissue using the instrument with a first surface area ratio of the active electrode relative to the return electrode;
using the means for changing to change to a second surface area ratio of the active electrode relative to the return electrode; and
using bipolar energy applied to the active electrode by the electrosurgical generator to treat tissue using the instrument with the second surface area ratio.

* * * * *